(12) United States Patent
Peterson et al.

(10) Patent No.: US 10,274,472 B2
(45) Date of Patent: Apr. 30, 2019

(54) SENSOR DEVICE FOR A HAZARDOUS WASTE CONTAINER

(71) Applicant: Nuclear Filter Technology, Inc., Golden, CO (US)

(72) Inventors: Michael D. Peterson, Parker, CO (US); Terry Wickland, Evergreen, CO (US); John L. Allbery, Denver, CO (US)

(73) Assignee: Nuclear Filter Technology, Inc., Golden, CO (US)

( * ) Notice: Subject to any disclaimer, the term of this patent is extended or adjusted under 35 U.S.C. 154(b) by 229 days.

(21) Appl. No.: 15/249,965

(22) Filed: Aug. 29, 2016

(65) Prior Publication Data
US 2017/0059501 A1 Mar. 2, 2017

Related U.S. Application Data

(60) Provisional application No. 62/210,644, filed on Aug. 27, 2015.

(51) Int. Cl.
*G01K 1/14* (2006.01)
*G01N 33/00* (2006.01)

(52) U.S. Cl.
CPC ............ *G01N 33/005* (2013.01); *G01K 1/14* (2013.01); *G01N 2033/0093* (2013.01)

(58) Field of Classification Search
CPC ............ G01K 13/02; G01K 1/14; G01K 1/08; G01K 2013/024; G01K 13/00; G01K 1/12; G01K 2205/02; G01K 17/00; G01K 1/024; G01K 1/143; G01K 1/022; G01K 7/01; G01N 25/00; G06K 19/0723; H01Q 1/2225; H01Q 1/243

USPC .................................................. 340/870.17
See application file for complete search history.

(56) References Cited

U.S. PATENT DOCUMENTS

| | | | |
|---|---|---|---|
| 3,547,350 A * | 12/1970 | Marcoux ............ | B23Q 11/1084 239/308 |
| 6,395,050 B1 | 5/2002 | Wickland et al. | |
| 6,557,428 B2 | 5/2003 | Wickland et al. | |
| 6,625,978 B1 * | 9/2003 | Eriksson ................. | F01N 3/023 60/278 |
| 9,448,090 B2 * | 9/2016 | Downie .................... | G01F 1/36 |
| 9,709,461 B2 * | 7/2017 | Lenferink ................ | G01K 1/14 |
| 2002/0062698 A1 * | 5/2002 | Baba ................... | G01L 19/0084 73/754 |

(Continued)

FOREIGN PATENT DOCUMENTS

| | | | | |
|---|---|---|---|---|
| DE | 4129697 A1 * | 3/1993 | ............ | G01N 1/2247 |
| EP | 470009 A * | 7/1990 | | |

*Primary Examiner* — Gail Kaplan Verbitsky
(74) *Attorney, Agent, or Firm* — Millen, White, Zelano & Branigan, P.C.; William Nixon (57) ABSTRACT

Information is obtained from a storage container that houses hazardous or potentially harmful waste. A sensor device is inserted into the container to allow a sensor using a sensor well to extend into the container. The sensor collects information on the conditions of the waste. The sensor well extends through a hole for a filter that vents gasses or vapors from the container. The sensor device also includes a housing with circuitry to perform the sensing as well as transmit and receive signals. In this manner, the sensor device transmits signals with information about the materials within the container for remote monitoring.

20 Claims, 10 Drawing Sheets

(56) References Cited

U.S. PATENT DOCUMENTS

| | | | | |
|---|---|---|---|---|
| 2003/0057152 A1* | 3/2003 | Haridas | ............... | C02F 3/282 |
| | | | | 210/603 |
| 2003/0102051 A1* | 6/2003 | Hasaka | ............... | F17C 13/04 |
| | | | | 141/325 |
| 2006/0064257 A1* | 3/2006 | Pennington | ............ | G01F 17/00 |
| | | | | 702/50 |
| 2009/0225808 A1* | 9/2009 | DiLeo | ............... | B01D 29/114 |
| | | | | 374/141 |
| 2011/0094296 A1* | 4/2011 | Burns | ............ | G01N 15/0205 |
| | | | | 73/64.56 |
| 2015/0360929 A1* | 12/2015 | O'Dougherty | ....... | B67D 7/0261 |
| | | | | 222/153.09 |
| 2016/0356425 A1* | 12/2016 | Fanger | ............... | F17C 11/007 |

* cited by examiner

SENSOR DEVICE FOR A HAZARDOUS WASTE CONTAINER

FIELD OF THE INVENTION

The present invention relates to the use of radio frequency (RF) tag technology in the remote continuous surveillance of the internal conditions for a container with hazardous waste, such as nuclear waste. More particularly, the present invention relates to a device that uses installed sensors to determine the conditions.

BACKGROUND OF THE RELATED ART

Material housed within containers may include hazardous materials. These materials may generate gasses or vapors that need to be vented from the container. One may wish to have knowledge of the composition, and other physical characteristics such as pressure, temperature and humidity, of the gasses or vapors so that decisions can be made with respect to the material of the container along with physical characteristics of the container, such as pressure, temperature and the like, so that decisions can be made that an over-pressure or temperature condition is eminent or is present. This is especially true if the gases or vapors are potentially harmful. Opening the container to check on the gasses or vapors may not be feasible.

SUMMARY OF THE INVENTION

The disclosed embodiments obtain internal sensor information, such as temperature, pressure, humidity, global positioning system data, and the like, from a sealed nuclear waste container. A sensor device may be used that includes a filter, sample port, or similar hardware equipped with an integrated sensor penetrating into the container. The sensor device also may include an intrinsically safe, active, sensor monitoring and radio frequency identification (RFID) communicating circuit in an integrated or attachable housing. The circuit will be capable of data logging sensor input from the container. Output of sensor data via remote communication may be transmitted to a computer monitoring location or a database storage.

A sensor device to sense a condition of materials within a container is disclosed. The sensor device may include a filter having a filter media and a hole. The gas from the container exits through the filter media and hole to a vent. The sensor device also includes a sensor within a sensor well that extends into the container through the hole. The sensor is configured to detect a condition of the gas within the container. The sensor device also includes a circuit to receive the data from the sensor and transmit a signal with the data. The sensor device also includes a housing to enclose the circuit and the sensor.

A method for using a sensor device to detect a condition of a gas within a container also is disclosed. The method includes flowing the gas through a filter attached to the container. The method also includes receiving the gas generated from material within the container into a sensor well. The sensor well extends into the container through a hole for the filter. The method also includes generating data about the gas from the sensor in the sensor well. The method also includes transmitting a signal using a circuit coupled to the circuit. The signal includes the data about the gas within the container.

A sensor device attached to a container of hazardous waste also is disclosed. The sensor device includes a housing including a radio frequency identification (RFID) circuit having an antenna and at least one sensor. The sensor device also includes a battery for the RFID circuit. The sensor device also includes a filter assembly to extend into the container. The filter assembly includes a thermocouple sensor coupled to the RFID circuit and a filter media. Gas from the container flows into the filter assembly so that the thermocouple sensor or the at least one sensor detects a condition of the gas. The RFID circuit is configured to send a signal including the data.

A container having the device also is disclosed. The device is mounted on the container using a bung or a self-tapping threaded device having an existing or installed filter assembly.

BRIEF DESCRIPTION OF THE DRAWINGS

The accompanying drawings are included to provide further understanding of the disclosed embodiments and constitute a part of the specification. The drawings listed below illustrate embodiments of the claimed invention and, together with the description, serve to explain the principles of the invention, as disclosed by the claims and their equivalents.

DESCRIPTION OF THE PREFERRED EMBODIMENTS

Aspects of the invention are disclosed in the accompanying description. Alternate embodiments of the present invention and their equivalents are illustrated without parting from the spirit or scope of the present invention. It should be noted that like elements disclosed below are indicated by like reference numerals and the drawings.

The disclosed embodiments implement monitoring technology around an active RFID platform. The disclosed device includes a thermocouple sealed sensor inside a housing that measures temperature and transmits the encrypted data to a receiver and a computer. The thermal data is then logged, tracked, and evaluated by the disclosed process. Thermal excursions may be measured. Upon detection of an event, alerts via email or messaging may be sent to a plurality of recipients. The dynamic temperature sensing may occur at set periods, such as daily, hourly, or every second, depending on a desired battery life.

The disclosed device may have an operable range between −40 degrees to 500 degrees Fahrenheit, when actively managed. Transmissions may be encrypted at 2.4 gigahertz (GHz). The transmissions may be made to gateway receivers over 1000 feet from the drums using the devices. The gateway receivers may relay communication to centrally managed centers or servers. These centers may message alerts if a potential harmful situation is detected. The RFID tag may provide individual drum identification with its encrypted signal such that the problem drum can be identified.

The disclosed device includes a sensor that senses hydrogen gas concentration in the head space. The device also may sense internal drum temperature, ambient temperature, pressure, relative humidity, and the like. The battery voltage also may be monitored. This data is sent to the receiver gateway at periodic times. For reference, a 3.5 volt battery may be used to power the RFID for a period of about 5 years when actively managed.

The device installed on the drums includes a sensor applicable to a wide range of waste site drum configurations—newly generated, vented, or unvented. Preferably, the device is installed into newly generated waste drums by threading the thermal sensor into the bung of the drum lid. Other embodiments may include the device installed into previously vented drums or unvented drums.

In order to communicate with the internal environment of the drum, the drum should be breached to test for temperature, pressure, gas analysis, and the like. The breaching of the drum in a nuclear waste environment has to be, at a minimum, rate for less than a 0.3 micron particle size release. To achieve this, the disclosed embodiments provide a sensor device that is fully sealed or able to have a HEPA rating for release. If HEPA rated, the disclosed device will allow the gas or pressure inside the drum to reach one or more sensors internal to the RFID housing or circuitry.

The disclosed embodiments include filters or ports designed to perform the functions either with a sealed tube or a sintered metal, carbon, or ceramic media. A circuit board housing has been designed to provide the necessary sealed electrical and pneumatic connections with the sensor tube, disclosed below.

Figure 1:
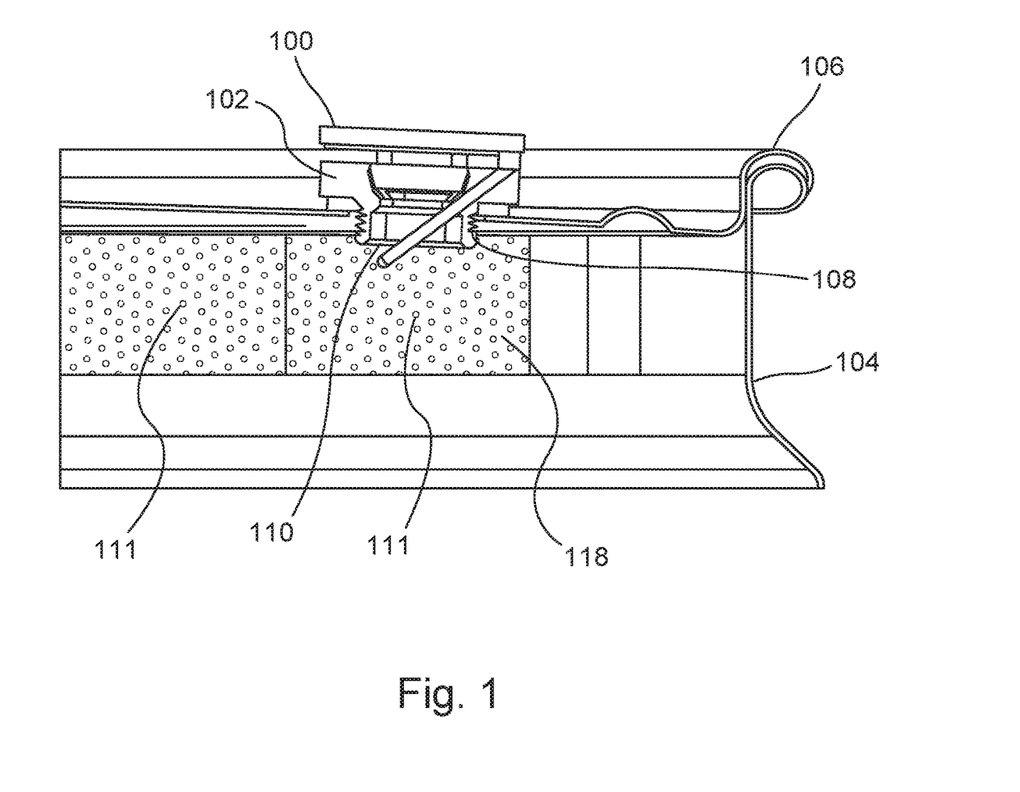
FIG. 1 illustrates a side view of a sensor device installed in a storage drum according to the disclosed embodiments.

FIG. 1 depicts a sensor device 100 installed in a storage drum 104 according to the disclosed embodiments. Components of sensor device 100 are disclosed in greater detail below. Sensor device 100 may provide information and feedback on materials stored in drum 104, such as gases and vapors 111. More preferably, storage drum 104 is a sealed nuclear waste container. Storage drum 104 also includes a top portion, or lid, 106 that seals the container from the outside. Although the term "storage drum" is used with relation to FIG. 1, it may be appreciated that any container can be used with the disclosed embodiments.

Sensor device 100 may be located in top portion 106. Specifically, sensor device 100 may be threaded into top portion 106 using a threaded bung 108 enclosing a hole 110. Threaded bung 108 preferably has a diameter of about ¾ to 2 inches. Alternatively, sensor device 100 may be drilled into top portion 106 using a self-threaded drill device. In other embodiments, sensor device 100 may be placed in another location of drum 104. Sensor device 100 has access to the interior of drum 104 via sensor well 202. As disclosed below, sensor well 202 includes a thermocouple sensor as well as other sensors to detect conditions of gases 111.

Sensor device 100 also may be placed with an existing filter, as disclosed in greater detail below. This configuration effectively seals the components of sensor device 100 and the materials within drum 104 from the outside.

Sensor device 100 includes filter 102. Filter 102 is placed under or alongside of sensor device, away from top portion 106. Filter 102 also may be referred to as a filter vent or plug. Filter 102 may include a filter media. Gases 111 within drum 104 may vent through filter 102. Gases 111 accumulates in head space 118 above the material within drum 104. Filter 102 removes particulate matter and compounds within the gas by trapping or absorbing the gases before it exits drum 104. In some embodiments, filter 102 may have a hexagonal shape.

Figure 2:
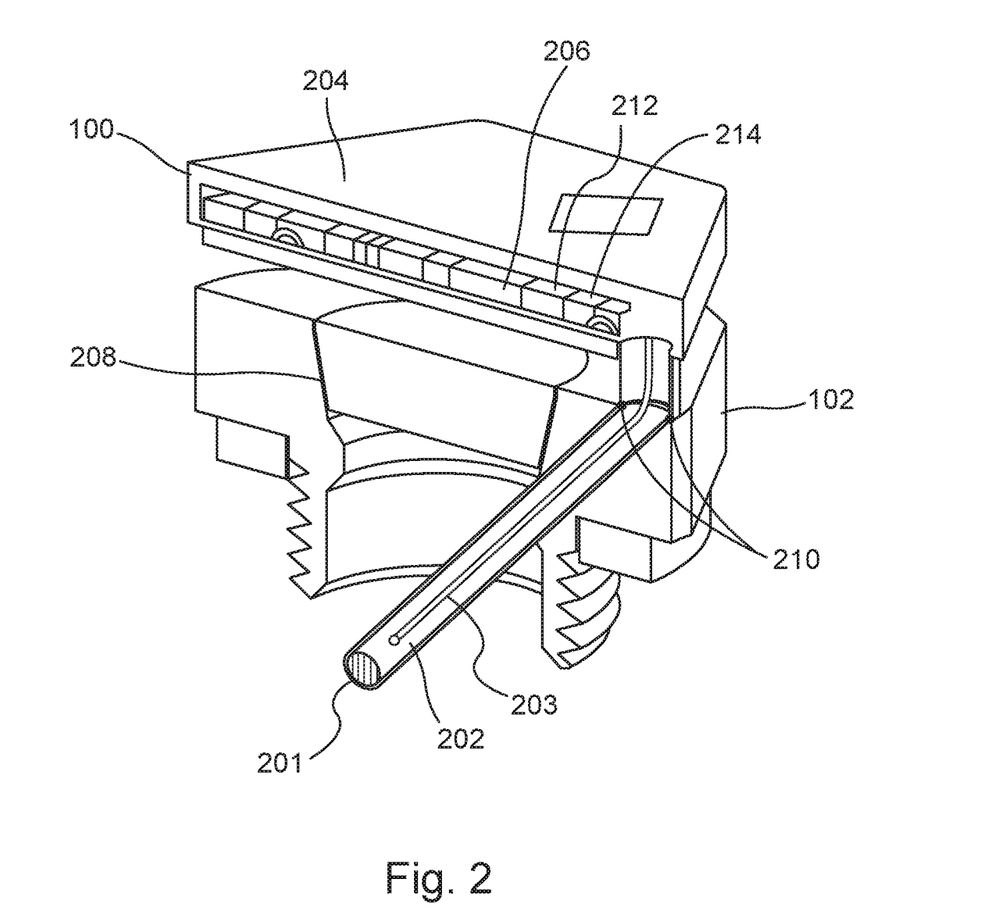
FIG. 2 illustrates a cut away view of a sensor device according to the disclosed embodiments.

FIG. 2 depicts a cut away view of sensor device 100 according to the disclosed embodiments. Filter 102 is shown having filter media 208, which may be any suitable material. For example, filter media 208 may be ceramic, carbon, sintered metals, and the like. Filter 102 may include different designs than those shown in FIGS. 1 and 2, as disclosed below. Filter 102 prevents the buildup of hydrogen, methane, and other flammable gases in drum 104, and also prevents possible deflagration.

Sensor device 100 also includes an integrated sensor well 202. Sensor well 202 extends into drum 104 through hole 110. Sensor well 202 may house and protect a thermocouple sensor 203 from exposure to the gases and other environmental factors within drum 104. Data about gases 111 is obtained by sensor 203. The type of sensor may vary and can include those used for the detection of conditions for hazardous materials. For example, types of sensors include, but are limited to, temperature, chemical detection, pressure, GPS, humidity, moisture, and the like. Further, the disclosed sensor 203 may be an infrared sensor.

Sensor device 100 also includes an RFID communicating circuit 206. Circuit 206 may have a unique RFID, or other identification means, to identify sensor device 100 as well as the associated storage drum 104. Circuit 206 may include an antenna to transmit a signal from sensor device 100. Circuit 206 also may include a power source to supply power to the circuit components. As shown in FIG. 2, circuit 206 is integrated with filter 102 and sensor well 202 within housing 204. Housing 204 is located on top of filter 102. Filter 102 should be in intimate contact with RFID circuit 206 for both electrical and pneumatic connections. Circuit 206 also may include gas sensor 212 and pressure sensor 214.

As shown, sensor well 202 allows thermocouple sensor 203 to detect a condition, preferably a temperature, of gases 111 that enter the sensor well. Gases 111 may enter through sealed or filtered end 201. If sensor well 202 includes a filtered endcap, such as end 201, then gases 111 are able to flow into the tube of sensor well 202 and to gas sensor 212 or pressure sensor 214 mounted with RFID circuit 206. Sensor well 202 also may include gas tight seal 210, if needed. Gas tight seal 210 may include a weld to seal sensor well 202.

This configuration allows for proper sensing of the conditions within drum 104. In order to interact with the internal environment to determine temperature, pressure, gas analytics, and the like of drum 104, it needs to be breached. The breaching of drum 104 in a nuclear waste environment has to be, at a minimum, rated for less than a 0.3 micron particle size release. In order to achieve this, sensor well 202 has to be fully sealed or able to have a HEPA rating for release. If HEPA rated, then sensor well 202 will allow gases 111 or the pressure inside drum 104 to reach the sensors internal to housing 204 of sensor device 100. Sensor device 100 has been designed to achieve this either with a sealed tube or a sintered metal, carbon, or ceramic media. RFID circuit 206 is designed to achieve the necessary sealed electrical and pneumatic connections with sensor well 202.

Gases 111 and pressure within drum 104 would have the same flow path. They would move up into filter 102 and into sensor well 202. Gases 111 and pressure pass through filter media 208 and into sealed housing 204. The appropriate sensor interacts with gases 111 or the pressure, then exhausts outside sealed housing 204. Thus, sensor device 100 provides a sealed component that extends into drum 104 to sense, detect, and determine conditions within the drum. Data related to these conditions may be transmitted from sensor device 100 using RFID circuit 206.

Figure 3:
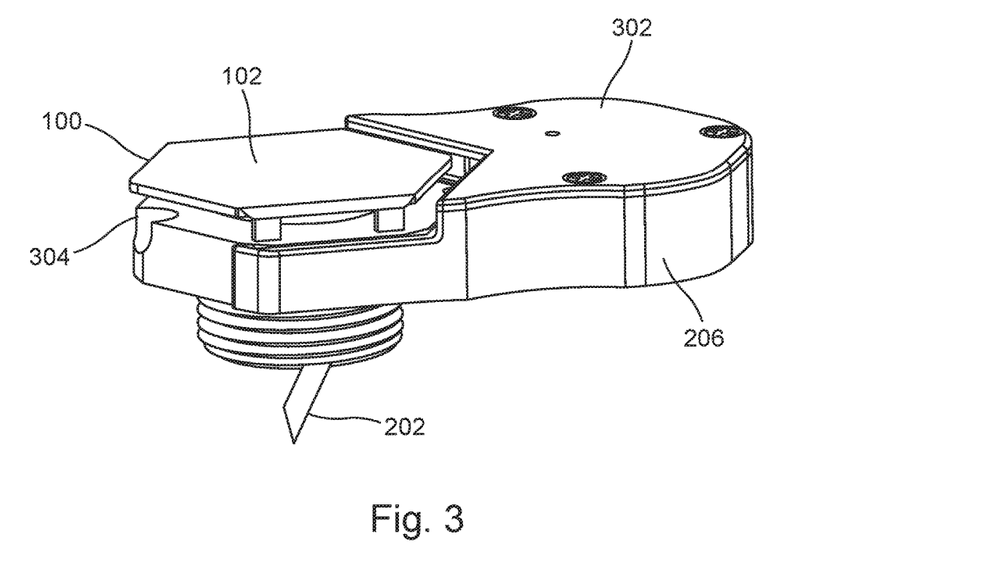
FIG. 3 illustrates a perspective view of the sensor device with an attachable housing according to the disclosed embodiments.
Figure 4:
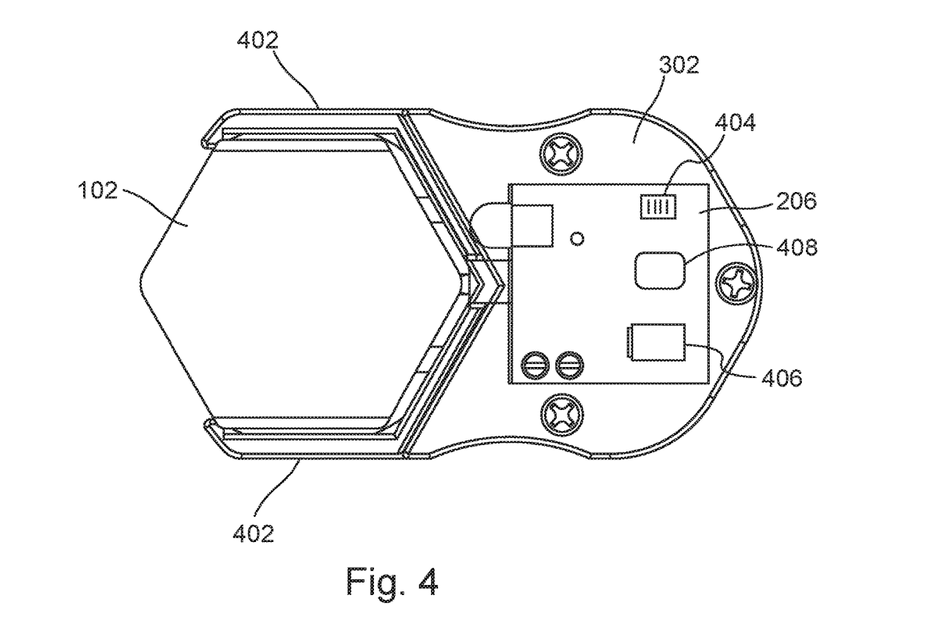
FIG. 4 illustrates a top view of the sensor device with an attachable housing according to the disclosed embodiments.

In other embodiments, the housing may be attached (and detached) from filter 102. This feature allows for removal or replacement of the circuit. FIG. 3 depicts a perspective view of sensor device 100 having attachable housing 302 according to the disclosed embodiments. FIG. 4 depicts a top view of sensor device 100 having attachable housing 302 according to the disclosed embodiments.

Filter 102 is shown along with vent 304 to allow gasses 111 to escape drum 104. Preferably, the gas vapors 111 flow through media filter 208. Sensor well 202 extends through hole 110 for filter 102 to detect information about the gasses 111 within drum 104. Preferably, sensor well 202 is integrated with filter 102.

Sensor device 100 attaches housing 302 for the sensors as well as RFID communication circuit 206 to filter 102. Arms 402 extend from housing 302 to attach to filter 102. Other embodiments may include an aperture created by joining arms 402 together to fit around filter 102. Arms 402 should not cover vents 304 so that gas may exit filter 102.

Circuit 206 may communicate to another device by generating a signal that is sent to a receiver. The signal may be relayed over a network to a monitor site or a database to store the information. Preferably, circuit 206 supports wireless protocols to transmit the signals containing the information. The signals may be transmitted using antenna 404 within circuit 206. Because of the size or possible limited power, signals from circuit 206 may not be receivable over a long distance. Thus, the signal from circuit 206 may be received by a router and then transmitted to a central monitoring location. Alternatively, circuit 206 may include a memory storage 408 that stores the information collected by the sensor for retrieval. Referring to the attached housing embodiment, housing 302 may be detached from filter 102 to allow access to the memory.

Sensor device 100 also may include battery 406 that supplies power to circuit 206. Battery 406 preferably is a lithium ion battery. Battery 406 also may power circuit 206 for a five year period when actively managed. Battery 406 may be a 3.5 volt battery. Battery 406 is sealed within the housing so that the whole unit may need to be replaced when the battery runs out of power. Battery life may depend on the information sample rate controlled within the system, as disclosed below.

The housing disclosed above may be comprises of material suitable to protect circuit 206 and any sensors, as well as withstand hazardous or outdoor conditions. Thus, the disclosed housings (housing 204 and attachable housing 302) may be made of hard plastic material. This material also should allow for the transmission and receipt of signals from circuit 206. Numerous housing styles and design may be implemented according to the disclosed embodiments.

FIGS. 5A-D depict a sensor device 100 that includes a housing 502 that attaches to an already existing filter dart 504 according to the disclosed embodiments. Other embodiments may have housing 502 coupled a drum vent system probe, disclosed in greater detail below. Filter dart 504 may already be installed on drum 104 to filter gases 111 as they exit. Filter dart 504 also may be known as a temperature dart to monitor the temperature of gases 111. Filter dart 504 includes an insertion end 506 that may break off after installation in drum 104. Threads 508 may hold filter dart 504 in place. Filter 510 receives gases 111 by a passage created once insertion end 506 is removed.

Figure 5A:
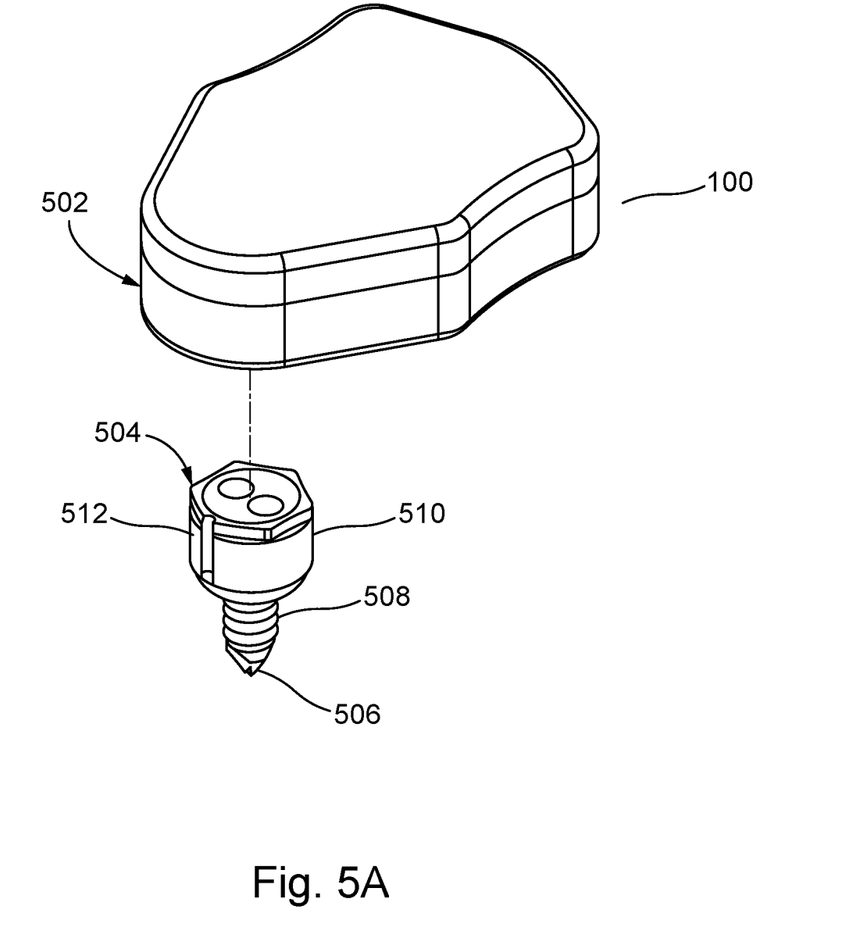
FIG. 5A illustrates a sensor device that includes a housing that attaches to an already existing filter dart according to the disclosed embodiments.

Housing 502 includes RFID communicating circuit 206 as well as a sensor to determine conditions of gases 111 exiting filter dart 504. As shown, housing 502 may be placed on top of filter dart 504 and coupled using a port having the shape of top portion 512 enclosing filter 510. Top portion 512 also may house the filter media for filter dart 504. In some embodiments, attachable housing 302 or housing 502 (disclosed below) is designed to mate with filter 102 or filter dart 504. The appropriate housing may be injection molded and hermetically sealed using ultrasonic welding. Housings 204, 302, or 502 are comprised of plastic material that can withstand outdoor conditions and a radiation environment.

Figure 5B:
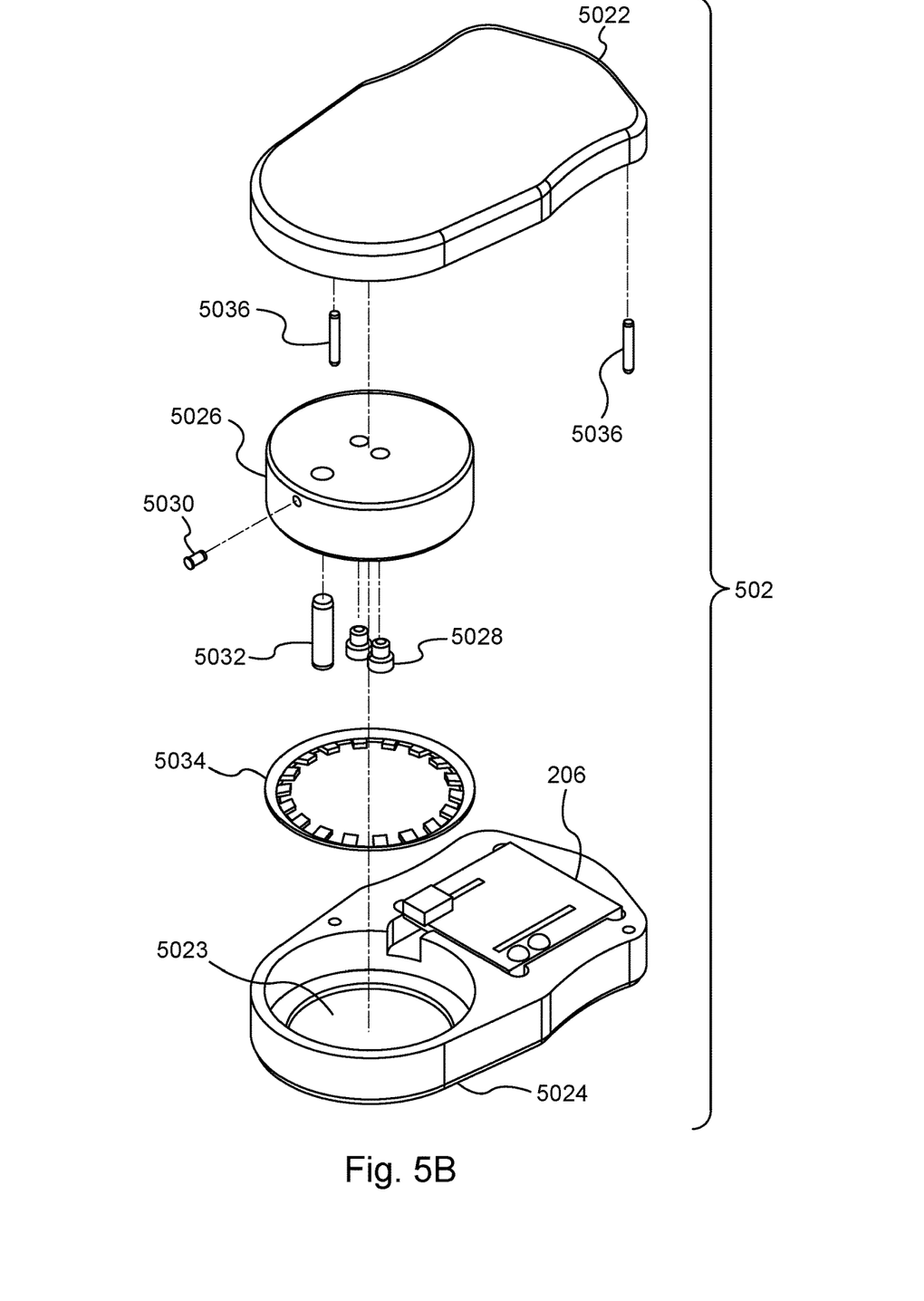
FIG. 5B illustrates an exploded view of the components within the housing.

Referring to FIG. 5B, an exploded view of sensor device 100 having housing 502 is disclosed. Housing 502 includes upper RFI housing 5022 that attached to lower RFI housing 5024. Recess 5023 in lower RFI housing 5024 is placed on top of filter dart 504 to form a seal such that gases 111 flow into housing 502. Recess 5023 holds contact insulator 5026 and external retaining ring 5034. Housing 502 also includes dart contact 5028 to couple with electrical contacts (shown below) within filter dart 504. Dowel pin 5030 may be inserted into contact insulator 5026 to position it within lower RFI housing 5024. Orientation dowel pin 5032 also may be inserted into contact insulator 5026. Dowel pins 5036 help connect upper RFI housing 5022 to lower RFI housing 5024. As shown, RFID circuit 206 along with the appropriate sensors and thermocouple data collection is enclosed within housing 502.

The arrangement of the components shown for housing 502 also may be used for the components within housing 204 and attachable housing 302. Differences do exist, such as sensor well 206 or arms 402, which attach the housings to the filter assemblies. Housing 204 may have thermocouple sensor 203 embedded within sensor device 100, while housings 302 and 502 attach to already existing thermocouple sensors.

Figure 5C:
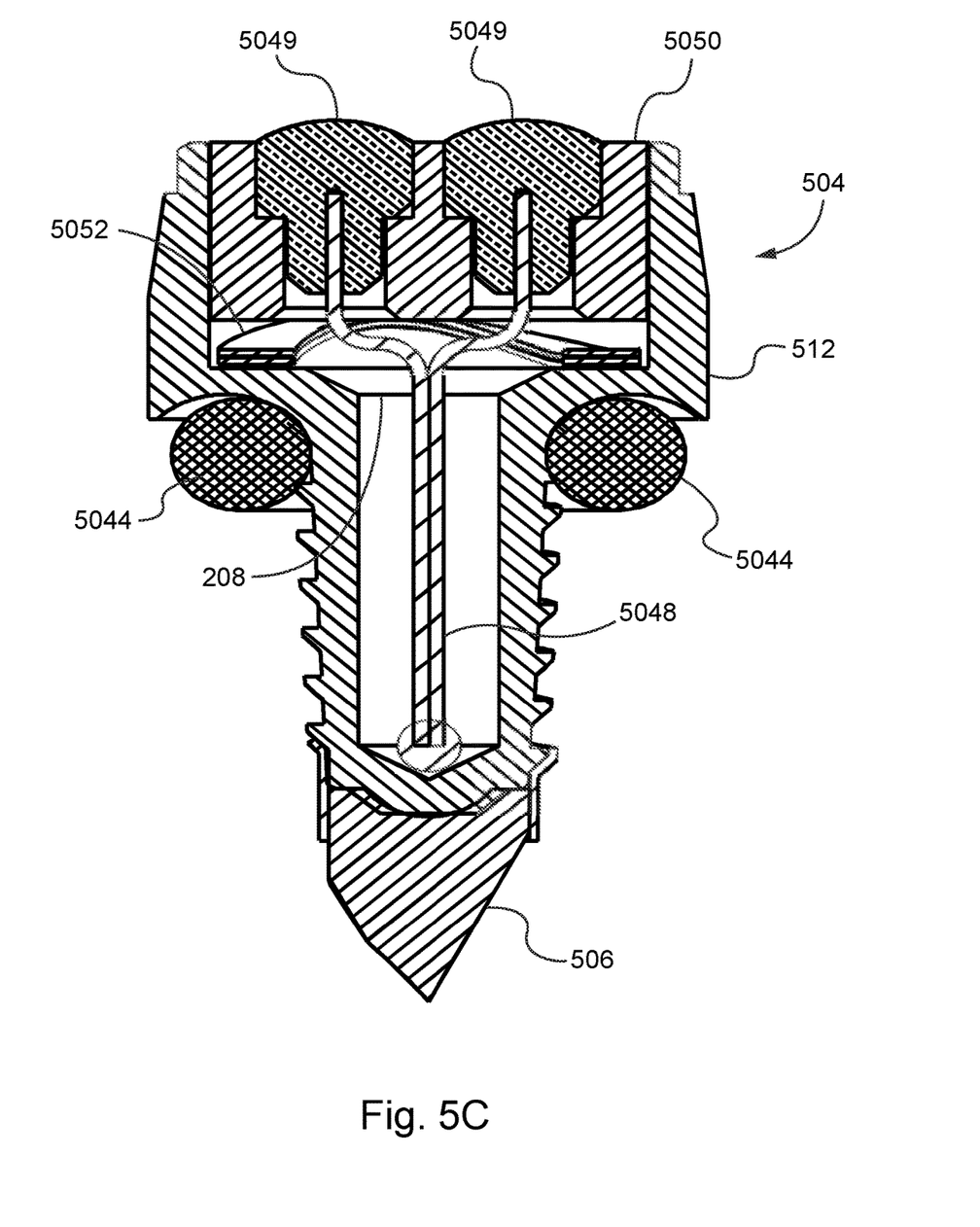
FIG. 5C illustrates a filter dart according to the disclosed embodiments.

FIG. 5C depicts a filter dart 504 according to the disclosed embodiments. As shown in FIG. 5A, filter dart 504 may be attached to housing 502 to form sensor device 100. In some embodiments, filter dart 504 is already installed in a drum 104. Alternatively, filter dart 504 may be installed and housing 502 connected to it.

Filter dart 504 includes insertion end, or tip, 506. Tip 506 may help pierce drum 104 as needed. Afterwards, tip 506 may separate from filter dart 504. In some embodiments, this may allow gases 111 to enter filter dart 504. In other embodiments, filter dart 504 is sealed. O-ring 5044 is located under top portion 512, which includes filter 510. Threads 508 also are shown.

Thermocouple sensor 5048 extends down into filter dart 504 into threaded section 508. Thermocouple sensor 5048 may act like thermocouple sensor 203 disclosed above in detecting a temperature of gases 111 within drum 104. Thermocouple sensor 5048 is connected to electrical contacts 5049 housed in insulation 5050. Electrical contacts 5049 may contact dart contact 5028 within housing 502. Spring washer 5052 is included in top portion 512. Filter media 208 also may be used in filter dart 504 in the event gases 111 are introduced internally for data collection.

Figure 5D:
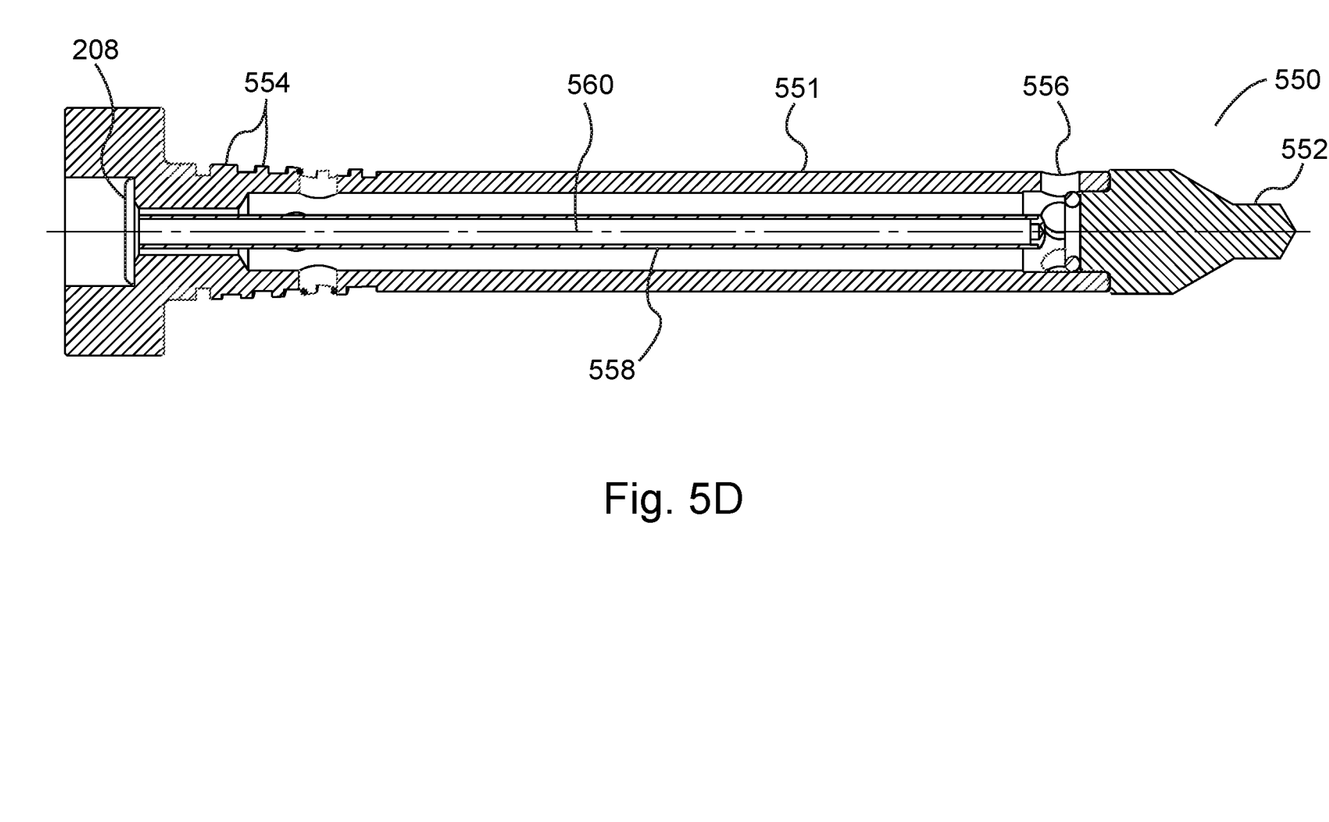
FIG. 5D illustrates a drum vent system type probe according to the disclosed embodiments.

FIG. 5D depicts a drum vent system type probe 550 according to the disclosed embodiments. Some drums may not be vented such that using a filter dart 504 is not practical. Sensor device 100 needs to be installed using probe 550 to pierce the drum to allow the thermocouple sensor access to gases 111 within the drum. Thus, housing 551 of probe 550 is designed for drilling through a drum lid, such as top portion 106 shown in FIG. 1, and then has self-tapping threads 554 attach to the lid. Housing 551 includes insertion end, or tip, 552. In some embodiments, insertion end 552 may not break off once probe 550 is installed.

Probe 550 includes thermocouple sensor 560 within tube 558. Tube 558 may protect sensor 560. Holes 556 in housing 551 allow air flow from drum 104 to permeate into probe 550 and expose gases 111 to tube 558. Tube 558 may be a filtered tube to allow gases 111 to flow to pressure or gas sensors in RFID circuit 206. Thermocouple sensor 560 may be connected to electrical contacts, such as contacts 5049 of filter dart 504. Thus, probe 550 may provide data on the conditions of gases 111 within drum 104. In some embodiments, filter media 208 may be included in probe 550.

Thus, the disclosed embodiments may use various "filter assemblies" to provide gases 111 to the appropriate thermocouple sensor as well as gas and pressure sensors. The filter assemblies may be incorporated into the housing for the RFID circuit and other components for sensor device 100. Alternatively, the filter assemblies may be separate from these housings, as shown in FIGS. 5A-D. The term filter assembly may encompass all these embodiments and includes the appropriate features to be inserted into a drum, extended into headspace 118 to analyze gases 111. One or more sensors within the filter assembly collects data that is sent by RFID circuit 206 to the appropriate location, as disclosed below.

Figure 6:
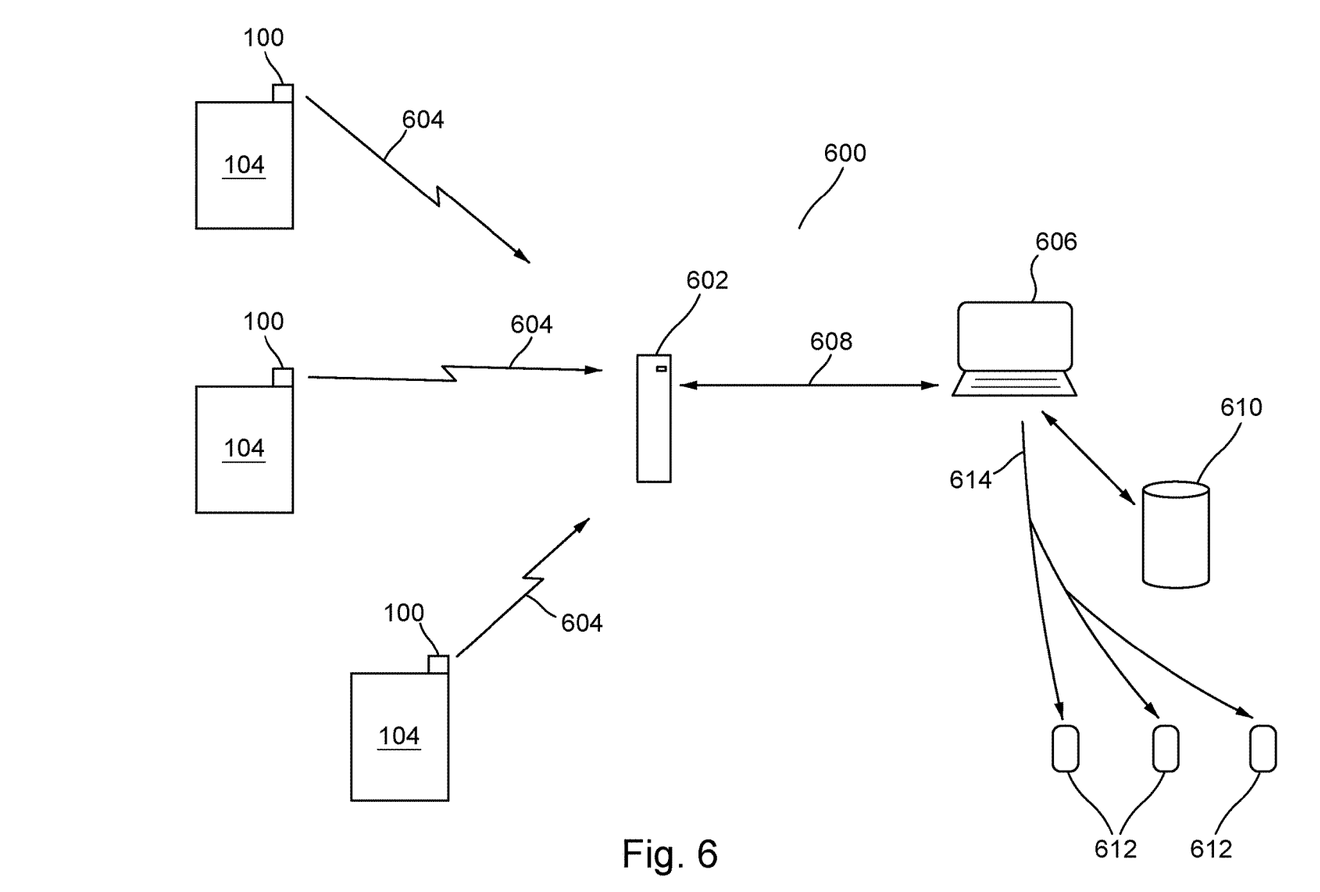
FIG. 6 illustrates a system for monitoring the conditions of a plurality of drums according to the disclosed embodiments.

FIG. 6 depicts a system 600 for monitoring drums 104 and transmitting alerts according to the disclosed embodiments. System 600 may represent some of the features used to monitor drums 104 and collect data on their conditions. System 600 may include other components not explicitly defined herein. System 600 uses sensor device 100 to monitor drums 104. Although only three drums 104 are shown, any number may be monitored, and, preferably, a large number, such as more than 30 drums, are monitored by system 600.

As disclosed above, sensor devices 100 collect data on the conditions of gases 111 within drums 104. Periodically, sensor devices 100 transmit this data using signals 604 to gateway receiver 602. Gateway receiver 602 may be located about 1000 feet from drums 104, such that signals 604 are received. Antennas 404 of circuits 206 send the information using encrypted transmissions.

Gateway receiver 602 sends the collected data using connection 608 to computing device 606. Computing device 606 includes a processor to execute operations using the data received from drums 104. Computing device may perform analysis and processes using the data to take further actions based on the data. These features are disclosed in greater detail below. For example, system 600 may use these components to alert authorities if a dangerous temperature change or other adverse condition occurs in a drum 104. Computing device 606 may communicate with server 610 to store data or to perform further operations. Computing device 606 may execute software having instructions to perform the functions disclosed herein.

If computing device 606 determines that a condition exists that may result in problems within a drum 104, then alerts 614 may be sent to devices 612 to inform personnel of the potential problem. Alerts 614 may be emails, text messages, and the like. Alternatively, computing device 606 may send a command to devices 612 to vibrate, make an audible sound, or other such action to notify personnel of a problem situation.

Computing device 606 using information received from gateway receiver 602 also may identify which drum 104 is having a problem due to the unique identification code provided by RFID circuit 206 within sensor device 100. Computing device 606 also may issue commands to drums 104 to provide additional information or to change their reporting periods. For example, if a problem is detected, computing device may command that sensor devices report every 30 seconds instead of every 5 minutes. Thus, if the condition disappears in a certain amount of time, then a false alarm may be reported.

Thus, once sensor device 100 is installed, the active RFID circuit 206 is snapped into place. A sensor connection is made and the fully encrypted transmission using signals 604 to gateway receiver is established. Using the unique code for each RFID circuit 206, computing device 606 may issue commands and instructions using gateway receiver 602 using encrypted signals.

One of the features of the disclosed embodiments is that a sensor device 100 may be installed into a wide range of drum configurations, such as newly generated, retrieved and unvented to fully characterized and ready for disposal. The disclosed embodiments provide a solution for thermal monitoring of waste drums. Further, the data and history collected by the sensor devices on the drums may provide valuable information for research and analysis as well as confidence in assuring safety. It is desired to demonstrate and prove that there are no adverse chemical reactions occurring inside a drum by monitoring, recording, trending, and analyzing each drum's thermal signature.

Each sensor device 100 within system 600 may measure the internal temperature of the drum head space, ambient temperature, ambient pressure, relative humidity, and the lithium battery voltage of battery 406. This data may be collected by system 600 and stored in server 610. These features allows for the collection of appropriate data of sufficient quality to verify internal drum conditions, establish when data requirements are satisfied, and allow for continuous improvement throughout project execution. The disclosed embodiments promote structured analysis, assumption verification, and completeness checks to attain a high probability that the collected data will meet project needs.

As disclosed above, the measurements collected by sensor devices 100 are transmitted to gateway receiver 602 at specified time intervals, ranging from every second to every day, or the like. Data may be captured digitally so that the logging and collecting a massive amount of data is possible. Data collection and transmission parameters may be set at computing device 606 and transmitted to sensor devices 100 in system 600.

The waste within drums 104 may vary. In other words, sets of drums 104 may include a variety of disposed materials that have a wide range of thermal characteristics. The different materials, therefore, may require different data and reporting frequencies. Once sensor devices 100 are installed on drums 104 and connections are made with gateway receiver 602, the disclosed embodiments are capable of changing the transmission frequency via a setting in gateway receiver 602. The collection parameters may be controlled during this process. The collected data may be displayed graphically on computing device 606 as well as devices 612.

Figure 7:
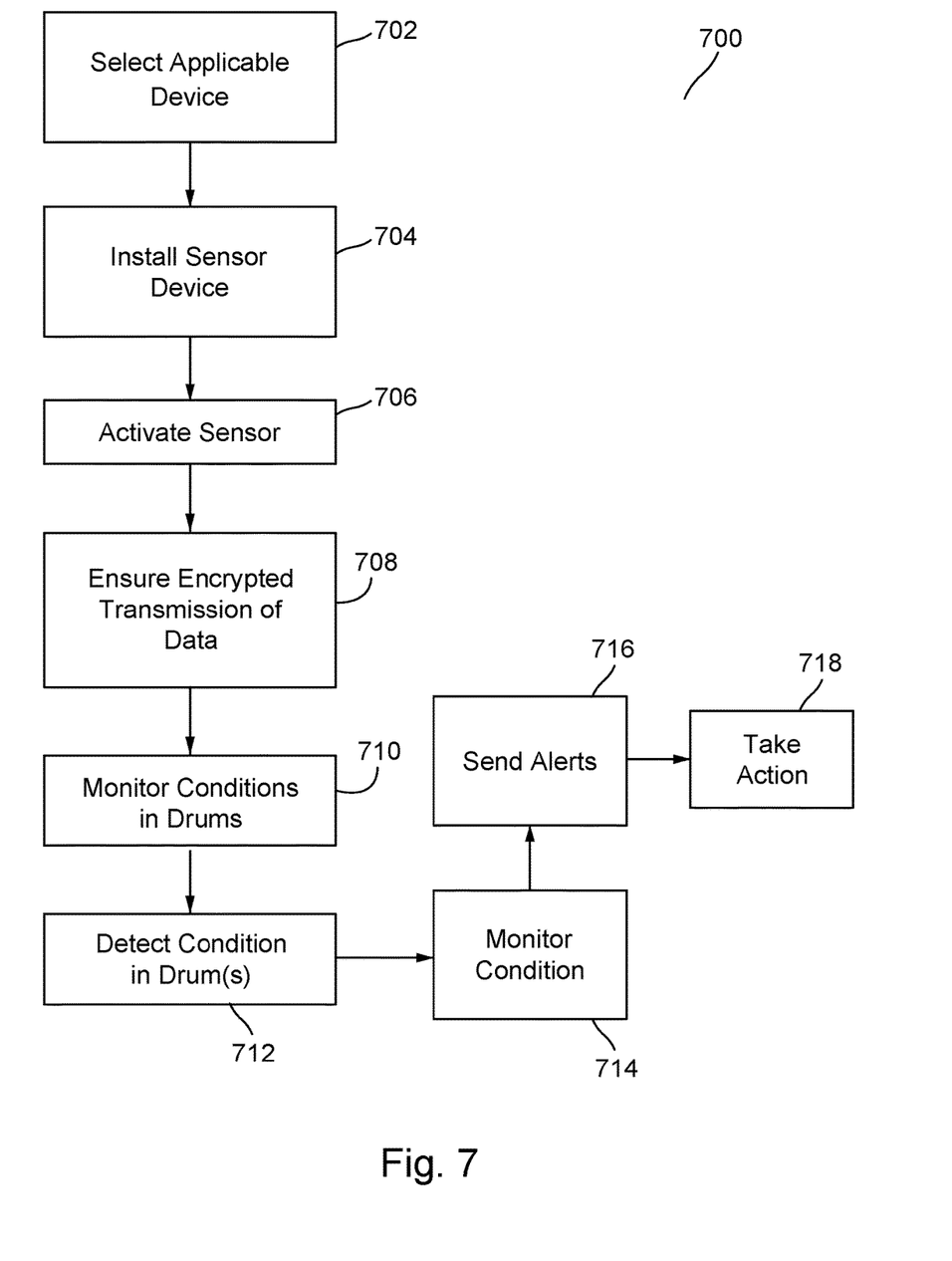
FIG. 7 illustrates a flowchart for using a sensor device within a system according to the disclosed embodiments.

FIG. 7 depicts a flowchart 700 for using a sensor device 100 within system 600 according to the disclosed embodiments. The process disclosed by flowchart 700 is one example of how the sensor devices may be installed and utilized in determining the condition of drums and reacting to any problems detected by the sensor devices. Additional steps may be included, but not described, that facilitate the use of the sensor devices. Further, not all steps need to be executed to perform the process disclosed by flowchart 700.

Step 702 executes by selecting the applicable sensor devices 100 for installation on drums 104. As disclosed above, various types of sensor devices 100 may be used. Sensor devices 100 may differ on how the filter is configured within the devices. For example, for newly installed drums, sensor device 100 may include the filter within the housing of the device along with the sensor well. These embodiments may be installed in the bung hole in the drum lids. Alternatively, sensor device 100 may be attached to existing filters in previously vented drums. Unvented drums may need a separate filter and sensor device assembly. Step 704 executes by installing sensor devices 100 on drums 104 according to the type determined in step 702.

Step 706 executes by activating sensor device 100. RFID circuit 206 and its antenna 404 is activated to send a signal confirming installation and activation. The signal includes a verification of a secured encrypted transmission as well as identification provided by RFID circuit 206 for the sensor device of the specific drum. Preferably, the signal is sent to gateway receiver 602. Step 708 executes by ensuring that the transmission of data is properly encrypted. Gateway receiver 602 may pass this information to computing device 606 so that the identification designations for each sensor device 100 and drum 104 are stored for reference.

Step 710 executes by monitoring conditions within drums 104 using sensor devices 100. Sensor devices 100 measure conditions of the gases within drums and send this information to gateway receiver 602 using RFID circuit 206. Step 712 executes by detecting a condition within a drum or drums using the information received. For example, the condition may be an increase in temperature of the gases within a drum 104 as detected by the corresponding sensor device 100. If the temperature goes above a set point for the materials within the drum, then the condition is detected by the data sent from RFID circuit 206.

Step 714 executes by monitoring the condition at the drum or drums to determine any change. For example, the temperature may return to normal after a period of time. Alternatively, the temperature may continue to increase above a safe level. If so, then step 716 executes by sending alerts to personnel using devices 612. Computing device 606 may facilitate determining when the alerts are sent. The alerts may be emails or text messages, or commands to cause an audible or haptic alert. Step 718 executes by taking action on the unsafe drum by personnel, including using the connection with system 600 to quickly identify the appropriate drum using the identification of RFID circuit 206.

Figure 8:
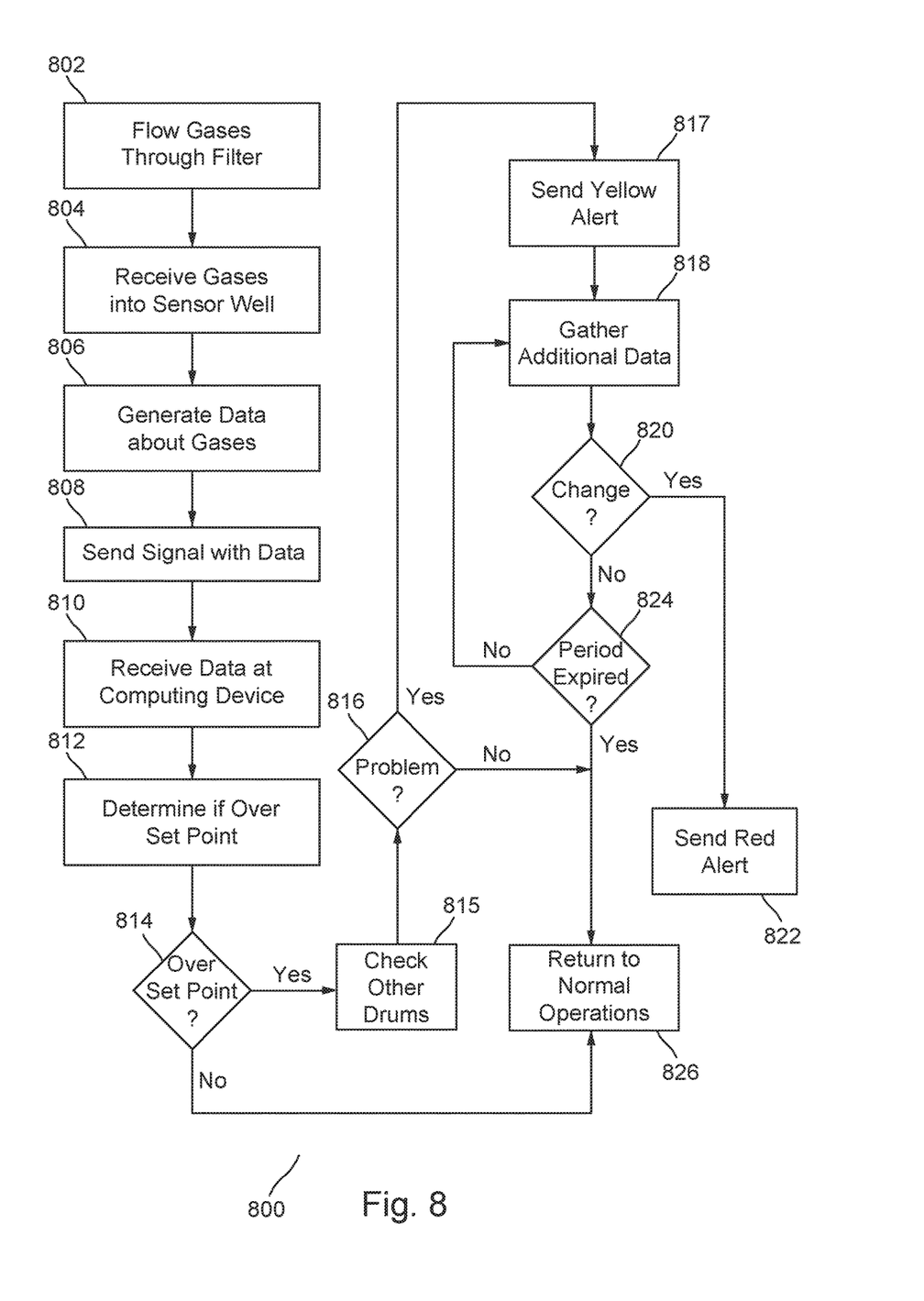
FIG. 8 illustrates a flowchart for monitoring a drum using a sensor device according to the disclosed embodiments.

FIG. 8 depicts a flowchart 800 for monitoring a drum 104 using a sensor device 100 within system 600 according to the disclosed embodiments. Flowchart 800 pertains to processes to monitor the conditions within a drum 104 and alert personnel if one is detected. Flowchart 800 may operate in conjunction with the process disclosed by flowchart 700.

Step 802 executes by flowing gases 111 through filter 102. Filter 102 is either part of or coupled to sensor device 100. Gases 111 may flow through filter media 208 and released out of vent 304. Step 804 executes by receiving gases 111 into sensor well 202. Sensor well 202 includes a sensor to determine one or more conditions of gases 111. The sensor detects the condition (temperature, pressure, chemical composition, and the like) and provides this data to RFID circuit 206. Step 806 executes by generating the data for the condition or conditions detected by the sensor. This data may be digital data having a value corresponding to the condition, such as temperature of the gas within sensor well 202.

Step 808 executes by sending signal 604 from RFID circuit 206 to gateway receiver 602 with the data. Signal 604, as disclosed above, is an encrypted transmission having a preferred frequency of 2.4 GHz. Step 810 executes by receiving the data at computing device 606 within system 600. Gateway receiver 602 may forward the received signal 604 to computing device 606. In some embodiments, gateway receiver 602 may encode the data within signal 604 for delivery to computing device 606.

Step 812 executes by determining whether the data received from sensor device 100 is over a set point for the monitored condition. A variety of materials may be stored within drums 104. Not every material should be at the same temperature or other parameter in a normal state. Thus, the disclosed embodiments will store the preferred conditions for various materials within the drums, such as on server 610. These reference set points are compared to the received data to determine whether a condition exists where the detected parameter is above or below a safe value for the condition. Using the temperature example, if the detected temperature is above a set point for a tolerable temperature, then a problem condition may exist in the drum. These set points may be adjusted or changed as needed.

Step 814 executes by determining whether the data for the detected condition is above the set point. Alternatively, step 814 may determine whether the data is below a set point, or outside a range. In short, step 814 determines whether the detected data does not meet a preferred value for the condition. If no, then flowchart 800 proceeds to step 826, disclosed in greater detail below.

If step 814 is yes, then step 815 executes by checking other drums within the group of the problem drum. The group may include drums within a specified vicinity of the identified drum or the entire group of drums. The check may include determining the conditions of the drums to see if they are over or near the set point. Computing device 606 may instruct sensor devices 100 of the appropriate drums 104 to detect and send the data for the condition. Step 816 executes by comparing the data received from drums 104 to the set point and determining whether a problem exists. If the other drums are maintaining under the set point, then a problem may exist in the drum above the set point. If step 816 is no, then flowchart proceeds to step 826.

If step 816 is yes, then step 817 executes by sending a yellow alert in system 600. The yellow alert lets others know that a possible problem exists within a drum 104. Other information, like the identification of the drum provided by the appropriate RFID circuit 206, may be provided. As disclosed above, the yellow alert may be sent as a text message or email to devices 612.

Step 818 executes by gathering additional information and data from drum 104 having the condition above the set point. For example, additional data points may be collected faster than the normal monitoring period. If the monitor is every 5 minutes, then computing device 606 may instruct RFID circuit 206 of the affected drum 104 to collect data every 30 seconds. Further, the additional data may be collected over a specified period of time, such as an hour. Step 820 executes by determining whether the additional collected data shows any change in the condition within drum 104. If the condition within drum 104 remains unchanged or returns to normal over this period, then the yellow alert may be called off. Step 820 may be executed every time additional data is received from drum 104.

If step 820 is yes, then step 822 is executed by sending a red alert within system 600. The change indicates that the situation has gotten worse within drum 104 and needs to be addressed before an accident occurs. The red alert is sent to device 612 via text message or email, or any other alert means, such as audible, visual, or haptic sensations. Computing device 606 may instruct RFID circuit 206 to collect data even more frequently.

If step 820 is no, then step 824 executes by determining whether the yellow alert monitoring period has expired. If no, then flowchart 800 proceeds back to step 818 to continue monitoring drum 104. If yes, then step 826 executes by returning RFID circuit 206 and sensor device 100 back to normal operations.

In some embodiments, the yellow alert steps may be skipped and flowchart 800 goes straight to sending a red alert within system 600. For example, the detected condition may have a value so high above the set point, that a hazardous accident is imminent. Thus, additional set points may be used according to these embodiments.

It will be apparent to those skilled in the art that various modifications and variations can be made in the disclosed alert system for a pool without departing from the spirit or scope of the invention. Thus, it is intended that the present invention covers these modifications and variations disclosed above provided that such modifications and variations come within the scope of any claims and their equivalents.

The invention claimed is:

1. A sensor device to sense a condition of materials within a container, the device comprising:
 a filter having a filter media and a hole, wherein gas from the container exits through the filter media and the hole to a vent;
 a sensor within a sensor well that extends into the container through the hole, wherein the sensor is configured to detect a condition of the gas within the container;
 a circuit to receive data from the sensor about the condition and transmit a signal with the data; and
 a housing to enclose the circuit and the sensor.

2. The sensor device of claim 1, wherein the circuit comprises a radio frequency identification (RFID) circuit.

3. The sensor device of claim 1, wherein the housing is configured to attach to the filter.

4. The sensor device of claim 1, wherein the sensor detects a temperature, pressure, humidity, or a chemical composition of the gas.

5. The sensor device of claim 1, wherein the filter and the housing have a hexagonal shape.

6. The sensor device of claim 1, wherein the sensor well is integrated with the filter.

7. The sensor device of claim 1, wherein the filter is within a filter dart attached to the housing.

8. The sensor device of claim 1, wherein the housing is hermetically sealed.

9. A method for using a sensor device to detect a condition of a gas within a container, the method comprising:
 flowing the gas through a filter attached to the container;
 receiving the gas generated from material within the container into a sensor well, wherein the sensor well extends into the container through a hole for the filter;
 generating data about the gas from a sensor within the sensor well; and
 transmitting a signal using a circuit coupled to the sensor, wherein the signal includes the data about the gas within the container.

10. The method of claim 9, further comprising storing the data using the circuit.

11. The method of claim 9, further comprising determining, with the sensor, a temperature, humidity, pressure, or a chemical composition of the gas.

12. The method of claim 9, further comprising encrypting the signal prior to transmission.

13. The method of claim 9, further comprising determining a problem within the container.

14. The method of claim 13, further comprising determining if the data indicates the problem within the container by comparing it to acceptable values for a normal condition.

15. The method of claim 13, further comprising sending an alert to a device about the problem within the container.

16. A sensor device attached to a container of hazardous waste, the sensor device comprising:
 a housing including a radio frequency identification (RFID) circuit having an antenna and at least one sensor;
 a battery for the RFID circuit; and
 a filter assembly to extend into the container, wherein the filter assembly includes a thermocouple sensor coupled to the RFID circuit and a filter media,
 wherein gas from the container flows into the filter assembly so that the thermocouple sensor or at least one sensor detects a condition of the gas, and
 wherein the RFID circuit is configured to send a signal including data about the condition of the gas.

17. The sensor device of claim 16, wherein the filter assembly is a filter dart.

18. The sensor device of claim 16, wherein the filter assembly is a probe.

19. The sensor device of claim 16, wherein the filter assembly includes a sensor well to enclose the thermocouple sensor.

20. The sensor device of claim 16, wherein the housing includes contacts to couple with contacts in the filter assembly.

* * * * *